(12) United States Patent
Lee et al.

(10) Patent No.: US 9,958,483 B2
(45) Date of Patent: May 1, 2018

(54) METHODS OF DETECTING CHANGE IN OBJECT AND APPARATUSES FOR PERFORMING THE METHODS

(71) Applicant: Samsung Electronics Co., Ltd., Suwon-si (KR)

(72) Inventors: Jaechun Lee, Seoul (KR); Ui Kun Kwon, Hwaseong-si (KR); Sang Joon Kim, Hwaseong-si (KR); Seungkeun Yoon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 204 days.

(21) Appl. No.: 14/864,154

(22) Filed: Sep. 24, 2015

(65) Prior Publication Data

US 2016/0291066 A1 Oct. 6, 2016

(30) Foreign Application Priority Data

Apr. 2, 2015 (KR) ........................ 10-2015-0046904

(51) Int. Cl.
| | |
|---|---|
| *G01R 27/28* | (2006.01) |
| *G01R 19/04* | (2006.01) |
| *A61B 5/00* | (2006.01) |
| *A61B 5/0402* | (2006.01) |
| *A61B 5/0488* | (2006.01) |
| *A61B 5/01* | (2006.01) |

(52) U.S. Cl.
CPC ............ *G01R 19/04* (2013.01); *A61B 5/0051* (2013.01); *A61B 5/01* (2013.01); *A61B 5/0402* (2013.01); *A61B 5/0488* (2013.01); *A61B 5/6801* (2013.01)

(58) Field of Classification Search
CPC ...... G01R 19/04; A61B 5/0051; A61B 5/6801
USPC .................................................. 324/616, 633
See application file for complete search history.

(56) References Cited

U.S. PATENT DOCUMENTS

| | | | |
|---|---|---|---|
| 4,688,580 | A | 8/1987 | Ko et al. |
| 6,013,075 | A | 1/2000 | Avramenko et al. |
| 8,428,683 | B2 | 4/2013 | Yoo et al. |
| 9,495,569 | B2 * | 11/2016 | Theurer ............. G06K 7/10366 |
| 2008/0180633 | A1 | 7/2008 | Yamada et al. |

(Continued)

FOREIGN PATENT DOCUMENTS

| | | |
|---|---|---|
| JP | 2010-240252 A | 10/2010 |
| JP | 2013-146437 A | 8/2013 |
| KR | 10-2004-0045364 A | 6/2004 |

(Continued)

OTHER PUBLICATIONS

Kim et al. "Compact Vital Signal Sensor Using Oscillation Frequency Deviatin"; IEEE Transactions on microwave theory and techniques, vol. 60 No. 2, Feb. 2012.*

(Continued)

*Primary Examiner* — Farhana Hoque
(74) *Attorney, Agent, or Firm* — NSIP Law

(57) ABSTRACT

A detecting apparatus includes a first resonator configured to generate a first resonance signal based on power output from a power supply in response to an object changing within a range of a field of the first resonator, a switch configured to connect the first resonator to the power supply in response to a control signal, and a controller configured to sample a value of an envelope of the first resonance signal to detect a change in the object.

20 Claims, 16 Drawing Sheets

(56) References Cited

U.S. PATENT DOCUMENTS

2012/0235634 A1* 9/2012 Hall .................. H03H 7/40
320/108

FOREIGN PATENT DOCUMENTS

KR   10-2009-0022085 A   3/2009
KR   10-2010-0128089 A   12/2010

OTHER PUBLICATIONS

Kim et al. "Compact Vital signal Sensor Using Oscillation Frequency Deviation", IEEE Transactions on Microwave Theory and Techniques, vol. 60, No. 2, Feb. 2012.*
S.-G. Kim et al., "Compact Vital Singal Sensor Using Oscillation Frequency Deviation," *IEEE Transactions on Microwave Theory and Techniques*, vol. 60, No. 2, Feb. 2012, pp. 393-400.
K.-y. Kim et al., "Non-Contact Vital Signal Sensor Based on Impedance Variation of Resonator," *The Journal of Korea Information and Communications Society*, vol. 38C, No. 9, Sep. 2013, pp. 813-821 (in Korean, including English abstract).

* cited by examiner

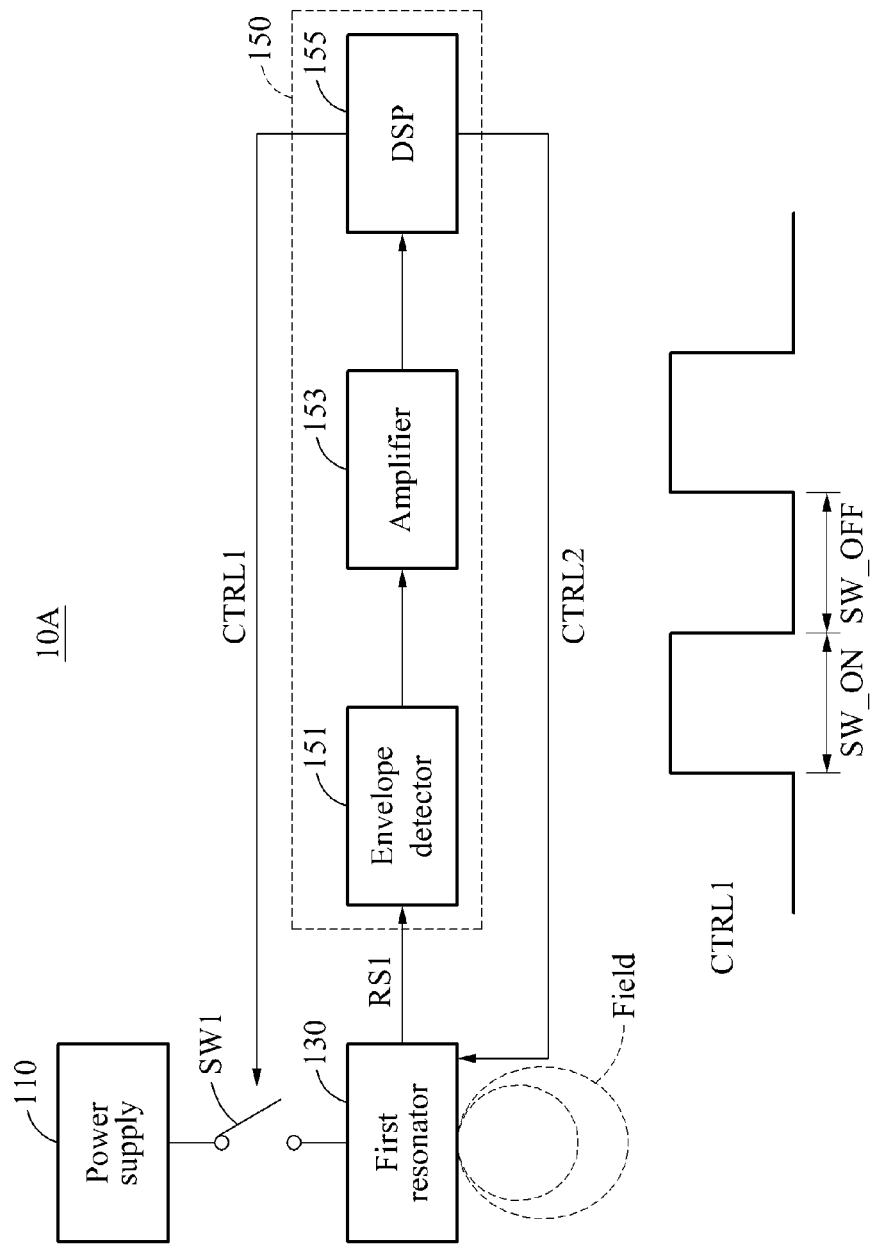

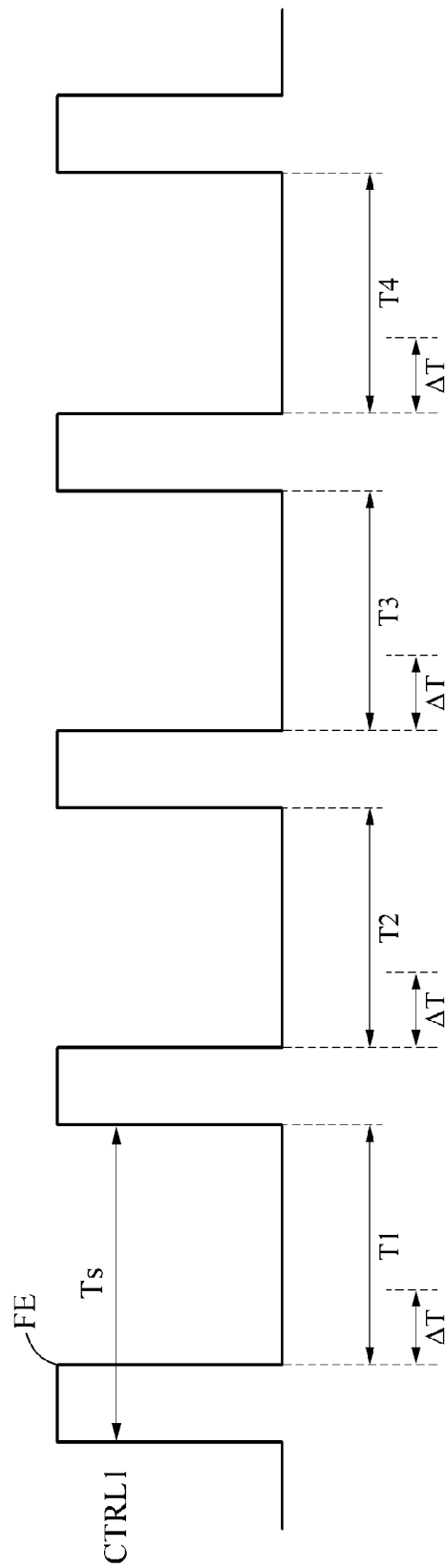

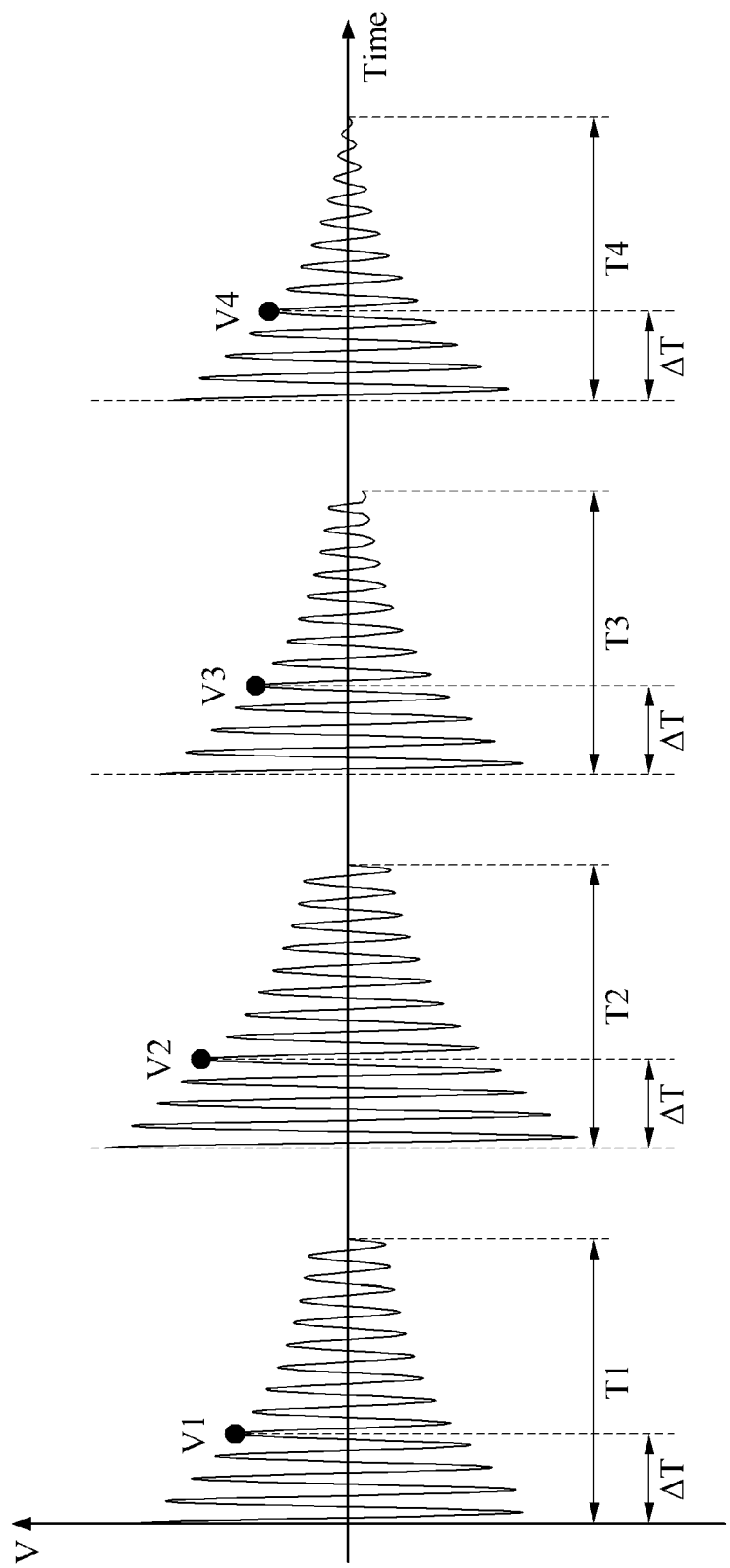

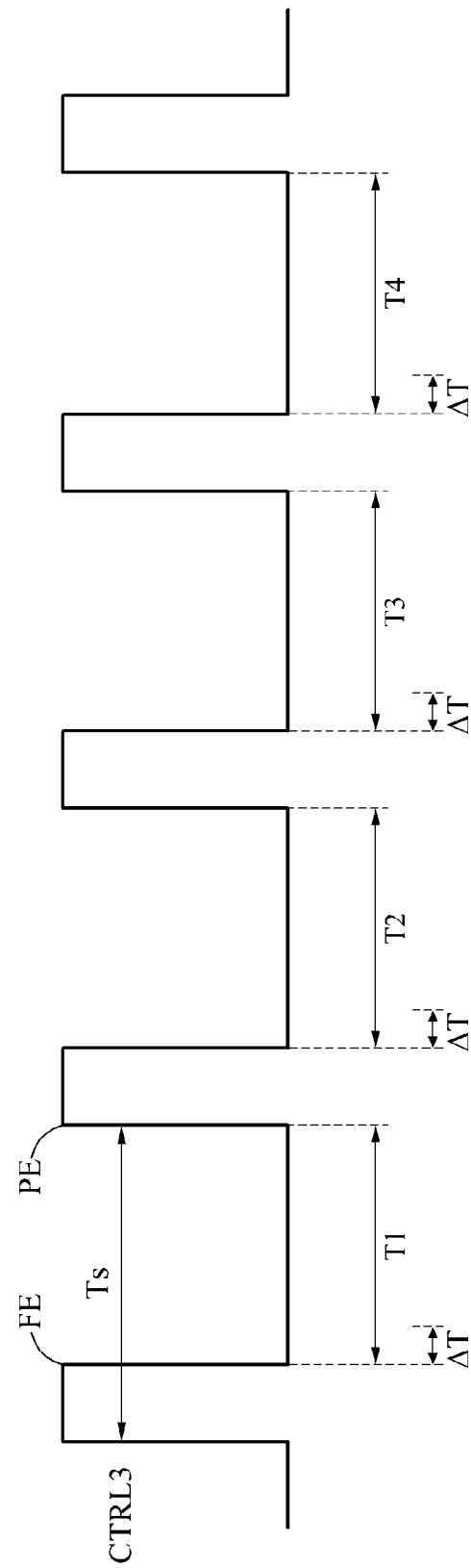

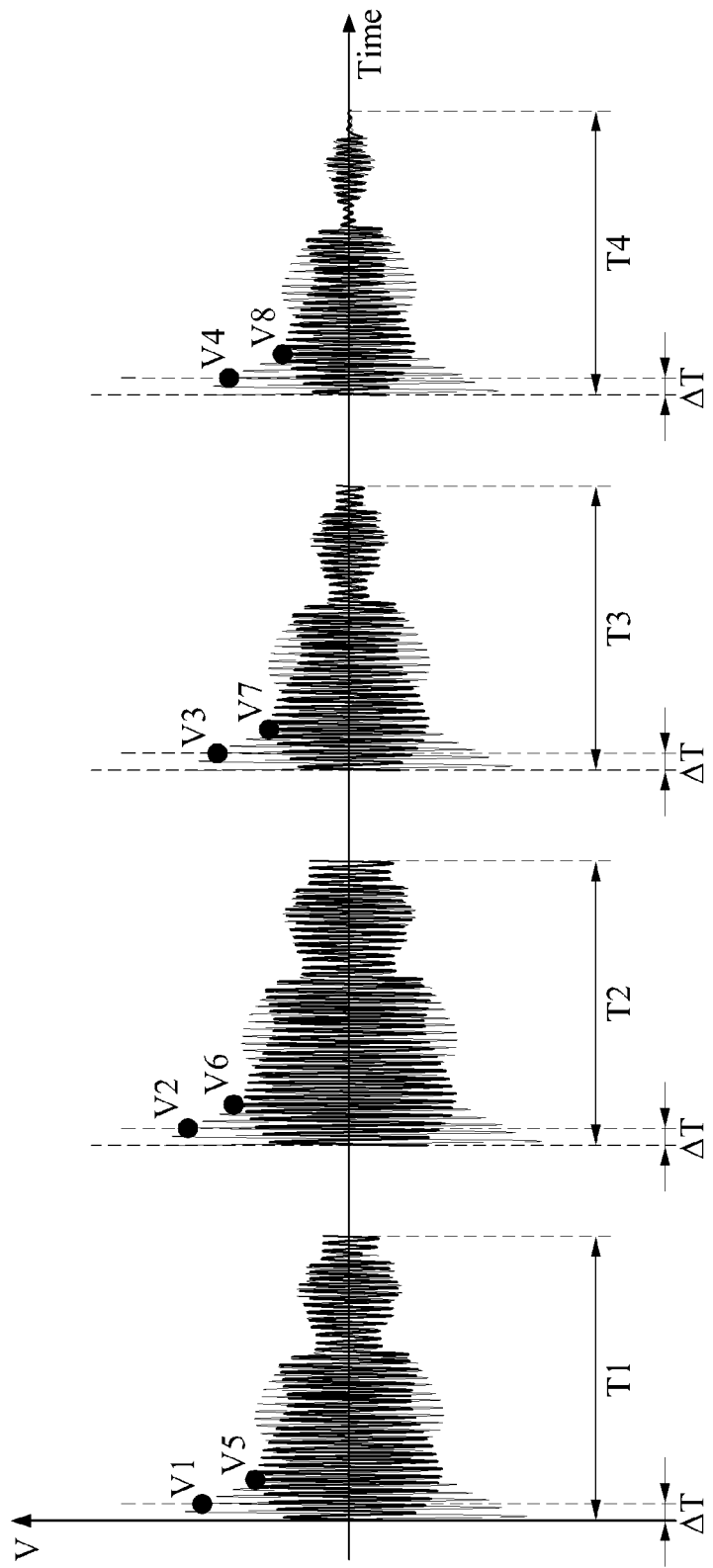

METHODS OF DETECTING CHANGE IN OBJECT AND APPARATUSES FOR PERFORMING THE METHODS

CROSS-REFERENCE TO RELATED APPLICATION(S)

This application claims the benefit under 35 USC 119(a) of Korean Patent Application No. 10-2015-0046904 filed on Apr. 2, 2015, in the Korean Intellectual Property Office, the entire disclosure of which is incorporated herein by reference for all purposes.

BACKGROUND

1. Field

The following description relates to a method of detecting a change in an object and apparatuses for performing the method.

2. Description of Related Art

To acquire biosignal information, for example, a heart rate or a respiratory rate, from an outside of a body, a technology using a near field may be used. The technology includes a scheme of detecting a change in a magnitude of an output signal based on a frequency characteristic of a filter and calculating a heart rate and a respiratory rate when an oscillation frequency changes due to a change in a characteristic of a resonant frequency of a resonator of an oscillator in response to a change in a body tissue in a near electromagnetic field of the resonator.

However, the scheme requires an oscillation circuit and a high quality filter to convert a change in the resonant frequency of the resonator to a change in a magnitude of a signal, and frequency characteristics of the resonator, the oscillation circuit, and the filter need to be well matched.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a detecting apparatus includes a first resonator configured to generate a first resonance signal based on power output from a power supply in response to an object changing within a range of a field of the first resonator; a switch configured to connect the first resonator to the power supply in response to a control signal; and a controller configured to sample a value of an envelope of the first resonance signal to detect a change in the object.

The controller may be further configured to sample the envelope of the first resonance signal at a predetermined point in time after a falling edge of the control signal, and acquire a value of the envelope of the first resonance signal at the predetermined point in time.

The controller may be further configured to calculate a period of a change in the acquired value of the envelope of the first resonance signal over time.

The detecting apparatus may further include a second resonator configured to induce a second resonance signal through a resonance between the first resonator and the second resonator; and the controller may be further configured to sample a value of an envelope of the second resonance signal to detect the change in the object.

The controller may be further configured to acquire a maximum value of the envelope of the second resonance signal by sampling the envelope of the second resonance signal in response to the control signal being deactivated.

The controller may be further configured to calculate a period of a change in the acquired maximum value of the envelope of the second resonance signal over time.

The controller may be further configured to change a resonant frequency of the first resonator to control the range of the field.

The controller may be further configured to sample the envelope of the first resonance signal, detect a noise component included in the first resonance signal, and control an activation time of the control signal based on the noise component.

The detecting apparatus may further include a second resonator configured to induce a second resonance signal based on the power output from the power supply; the switch may be further configured to connect one of the first resonator and the second resonator to the power supply in response to the control signal; and the controller may be further configured to sample a value of an envelope of a resonance signal output from one of the first resonator and the second resonator to detect the change in the object.

In another general aspect, a detecting apparatus includes a first resonator configured to generate a first resonance signal based on power output from a power supply in response to an object changing within a range of a field of the first resonator; a switch configured to connect the first resonator to the power supply in response to a control signal; a second resonator configured to induce a second resonance signal through a resonance between the first resonator and the second resonator; and a controller configured to sample a value of an envelope of either one or both of the first resonance signal and the second resonance signal to detect a change in the object.

The controller may be further configured to sample an envelope of the first resonance signal at a predetermined point in time after a falling edge of the control signal, and acquire a value of the envelope of the first resonance signal at the predetermined point in time.

The controller may be further configured to acquire a maximum value of an envelope of the second resonance signal by sampling the envelope of the second resonance signal in response to the control signal being deactivated.

The controller may be further configured to change a resonant frequency of the first resonator to control the range of the field.

The controller may be further configured to sample an envelope of either one or both of the first resonance signal and the second resonance signal to detect a noise component included in either one or both of the first resonance signal and the second resonance signal, and control an activation time of the control signal based on the noise component.

In another general aspect, a method of detecting a change in an object includes connecting a first resonator to a power supply in response to a control signal; generating, using the first resonator, a first resonance signal based on power output from the power supply in response to the object changing within a range of a field of the first resonator; and sampling a value of an envelope of the first resonance signal to detect a change in the object.

The sampling may include sampling the envelope of the first resonance signal at a predetermined point in time after a falling edge of the control signal; and acquiring a value of the envelope of the first resonance signal at the predetermined point in time.

The method may further include calculating a period of a change in the acquired value of the envelope over time.

The method may further include inducing a second resonance signal, using a second resonator, through a resonance between the first resonator and the second resonator; and sampling a value of an envelope of the second resonance signal to detect the change in the object.

The sampling of the value of the envelope of the second resonance signal includes acquiring a maximum value of the envelope of the second resonance signal by sampling the envelope of the second resonance signal in response to the control signal being deactivated.

The method of claim may further include calculating a period of a change in the acquired maximum value of the envelope of the second resonator over time.

Other features and aspects will be apparent from the following detailed description, the drawings, and the claims.

BRIEF DESCRIPTION OF THE DRAWINGS

FIG. 1 illustrates an example of a detecting apparatus.

FIG. 2A is a timing diagram of an example of a control signal output to a switch of FIG.

FIG. 2B is a graph provided to explain examples of envelopes of a first resonance signal generated based on the control signal of FIG. 2A.

FIG. 4A is a timing diagram of an example of a control signal output to a switch of FIG. 3.

FIG. 4B is a graph provided to explain examples of envelopes of a first resonance signal and a second resonance signal generated based on the control signal of FIG. 4A.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 2C:
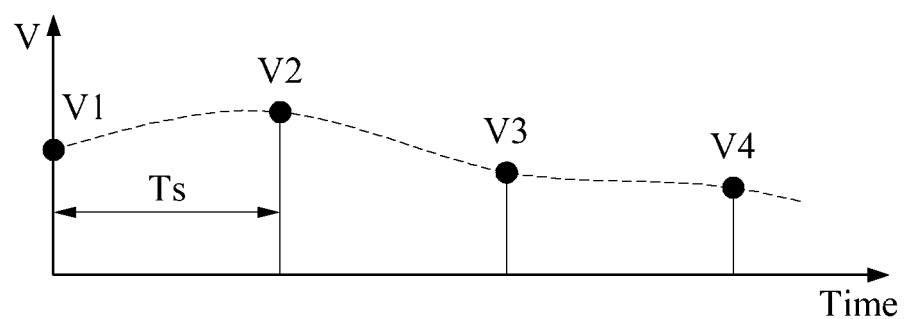
FIG. 2C is a graph provided to explain an example of a period of a change in values acquired from the envelopes of FIG. 2B at regular intervals over time.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

In this application, a detecting apparatus is an apparatus for detecting a change in an object within a range of a field of a resonator. The change in the object may include a change in a static movement or a dynamic movement of the object. The static movement indicates that the object hardly moves at a predetermined position. The dynamic movement indicates that the object moves at a predetermined position or moves from one position to another position.

The detecting apparatus detects a change in a magnitude of a resonance signal generated by a resonator and detects a change in an object within a range of a field of the resonator. The magnitude of the resonance signal may be, for example, a value of an envelope of the resonance signal. The value of the envelope may be, for example, an amplitude of the envelope. The object may include an animate object (for example, a human) and an inanimate object (for example, a transportation vehicle). In one example, the object may be a body tissue of a human, for example, a heart, a lung or a blood vessel of the human. The body tissue may be, for example, an epithelial tissue, a connective tissue, a cartilaginous tissue, an osseous tissue, a muscular tissue, a nervous tissue, blood, or lymph or any other body tissue. When a body tissue of a human, for example, a heart, a lung, or a blood vessel is within a range of a field of a resonator, the detecting apparatus detects a change in a value of an envelope of a resonance signal generated by the resonator due to a change in the body tissue, detects the change in the body tissue, calculates a period of the detected change in the value of the envelope, and detects or acquires the calculated period as a biosignal, for example, a heart rate, a respiratory rate, or a pulse rate.

In other words, when an object changes within a range of a field of a resonator, the detecting apparatus detects a change in the object based on a resonance signal generated by the resonator, and detects a period of the change in the object. For example, when an object is a human, the detecting apparatus detects a biosignal from the human. In this example, the biosignal may be any type of signal that may be measured, monitored, or detected in a continual, intermittent, or one-time manner from a biological being, and may be unique for each biological being. The biosignal may be, for example, an electrocardiogram (ECG), an electromyogram (EMG), a temperature, a humidity, an atmosphere, or a momentum.

In one example, the detecting apparatus is implemented as an independent apparatus. In this example, the detecting apparatus is applicable in various ways. For example, the detecting apparatus may be wearable on a user. The detecting apparatus may include, for example, all wearable devices capable of or suitable for being worn by users. Additionally, the detecting apparatus may be installed in a predetermined object. The object may be, for example, a moving object, for example a transportation vehicle, or a stationary object, for example, a building.

In another example, the detecting apparatus is implemented as a printed circuit board (PCB) (for example, a motherboard), an integrated circuit (IC), or a system on chip (SoC), and is embedded in an electronic apparatus. The electronic apparatus may be implemented as a personal computer (PC), a data server, or a portable apparatus.

The portable apparatus may be implemented as a laptop computer, a mobile phone, a smart phone, a tablet PC, a mobile Internet device (MID), a personal digital assistant (PDA), an enterprise digital assistant (EDA), a digital still camera, a digital video camera, a portable multimedia player (PMP), a personal navigation device or a portable navigation device (PND), a handheld game console, an e-book, or a smart device.

The smart device may be implemented as a smart watch or a smart band.

FIG. 1 illustrates an example of a detecting apparatus 10A.

Referring to FIG. 1, the detecting apparatus 10A includes a power supply 110, a switch SW1, a first resonator 130, and a controller 150.

The detecting apparatus 10A detects a magnitude of a resonance signal generated from a resonator, and detects a change in an object within a range of a field of the resonator. The magnitude of the resonance signal may be, for example, a value of an envelope of the resonance signal.

The power supply 110 supplies power to the first resonator 130. For example, when the power supply 110 is connected to the first resonator 130 via the switch SW1, the power supply 110 supplies power to the first resonator 130. The power supply 110 may be, for example, either a direct current (DC) voltage source or a DC source.

The switch SW1 is turned on or off in response to a control signal CTRL1. For example, the switch SW1 is turned on in response to the control signal CTRL1 being activated, as indicated by SW_ON of FIG. 1, and is turned off in response to the control signal CTRL1 being deactivated, as indicated by SW_OFF of FIG. 1.

The switch SW1 controls a connection between the power supply 110 and the first resonator 130 in response to the control signal CTRL1. In one example, when the switch SW1 is turned on in response to the control signal CTRL1 being activated, the power supply 110 and the first resonator 130 are connected to each other. In another example, when the switch SW1 is turned off in response to the control signal CTRL1 being deactivated, the power supply 110 and the first resonator 130 are disconnected from each other.

The first resonator 130 generates a first resonance signal RS1 based on the power output from the power supply 110. The first resonator 130 may be, for example, a resonator configured to generate an electric field in the form of a capacitor, or a resonator configured to generate a magnetic field in the form of an inductor.

The first resonator 130 generates the first resonance signal RS1 through charging and discharging. In one example, when the switch SW1 is turned on in response to the control signal CTRL1 being activated, the power supply 110 and the first resonator 130 are connected to each other, and the first resonator 130 is charged. In another example, when the switch SW1 is turned off in response to the control signal CTRL1 being deactivated, the power supply 110 and the first resonator 130 are disconnected from each other, and the first resonator 130 starts discharging. In this example, the first resonator 130 generates the first resonance signal RS1 during the discharging.

The first resonator 130 outputs the first resonance signal RS1 to the controller 150.

Figure 6:
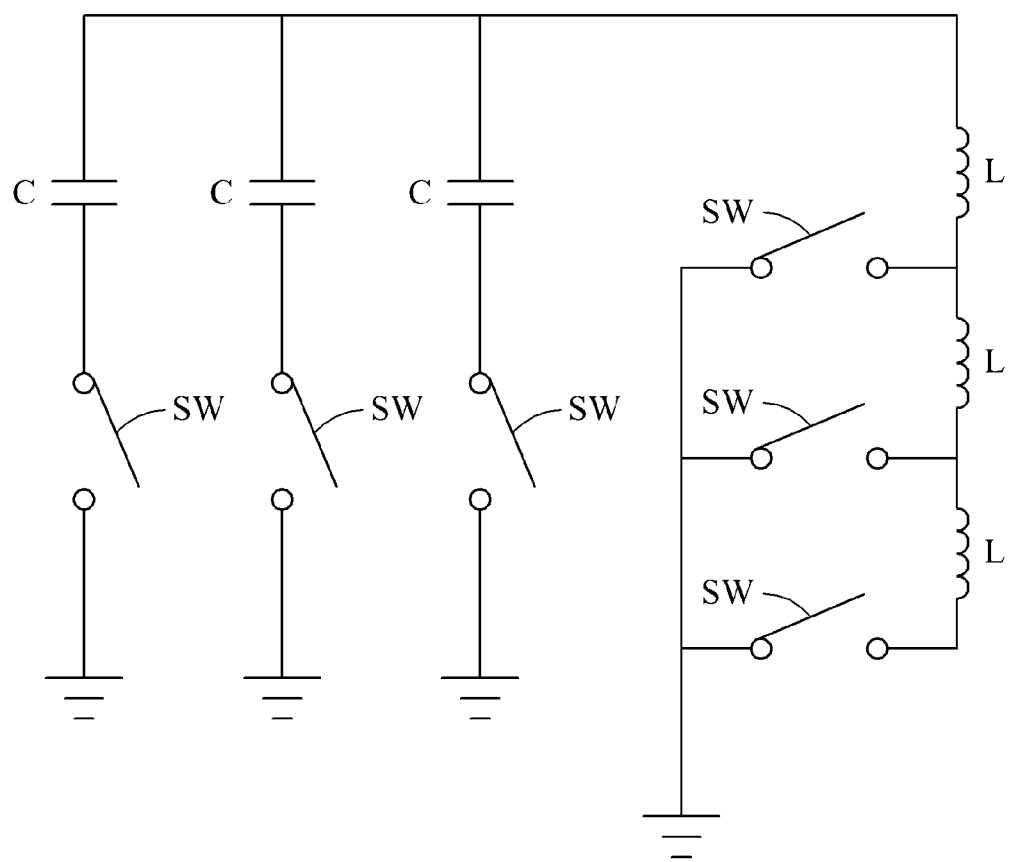
FIG. 6 illustrates an example of a circuit of a resonator included in the detecting apparatuses of FIGS. 1, 3, and 5.

The first resonator 130 changes a resonant frequency in response to a control signal CTRL2. Accordingly, a range of a field of the first resonator 130 may be adjusted. The first resonator 130 may be, for example, a variable resonator. Referring to FIG. 6, a variable resonator includes three capacitors C, three inductors L, and six switches SW, but this is merely one example, and there may be different numbers of capacitors C, inductors L, and switches SW. For example, the variable resonator may include a plurality of capacitors C, a plurality of inductors L, and a plurality of switches SW. The control signal CTRL2 controls the switches SW to change the resonant frequency of the first resonator 130.

The controller 150 controls an overall operation of the detecting apparatus 10A. The controller 150 controls the power supply 110, the first resonator 130 and the switch SW1 in the detecting apparatus 10A.

The controller 150 processes the first resonance signal RS1. The controller 150 includes an envelope detector 151, an amplifier 153, and a digital signal processor (DSP) 155.

The envelope detector 151 detects an envelope of the first resonance signal RS1. The envelope detector 151 outputs the detected envelope to the amplifier 153.

The amplifier 153 amplifies the envelope of the first resonance signal RS1. The amplifier 153 outputs the amplified envelope to the DSP 155. In application, amplifying an envelope includes, for example, amplifying a value of the envelope.

The DSP 155 samples the amplified envelope of the first resonance signal RS1. The DSP 155 calculates a period of a change in a value of the envelope of the first resonance signal RS1 over time based on the sampled envelope. When an object changes within the range of the field of the first resonator 130, the DSP 155 detects or acquires the period of the change in the value of the envelope of the first resonance signal RS1 over time as a period of a change in the object.

The DSP 155 changes a resonant frequency of the first resonator 130 to control the range of the field of the first resonator 130. For example, the DSP 155 generates a control signal CTRL2 to control a change in the resonant frequency of the first resonator 130, and may outputs generated control signal CTRL2 to the first resonator 130.

The DSP 155 samples the envelope of the first resonance signal RS1, detects a noise component included in the first resonance signal RS1, and controls an activation time of the control signal CTRL1 based on the detected noise component. In response to the activation time of the control signal CTRL1 being controlled, the range of the field of the first resonator 130 is adjusted. In one example, when the activation time of the control signal CTRL1 is controlled to increase, the first resonator 130 is connected to the power supply 110 during a relatively long period of time, is charged with a large amount of power or energy, and generates a first resonance signal RS1 with a greater magnitude. In another example, when the activation time of the control signal CTRL1 is controlled to decrease, the first resonator 130 is connected to the power supply 110 during a relatively short period of time, is charged with a small amount of power or energy, and generates a first resonance signal RS1 with a smaller magnitude.

Hereinafter, an operating method of the detecting apparatus 10A to detect a change in an object within the range of the field of the first resonator 130 is further described with reference to FIGS. 2A, 2B, and 2C.

FIG. 2A is a timing diagram of an example of the control signal CTRL1 output to the switch SW1 of FIG. 1, and FIG. 2B is a graph provided to explain examples of envelopes of a first resonance signal generated based on the control signal CTRL1 of FIG. 2A. FIG. 2C is a graph provided to explain an example of a period of a change in values acquired from the envelopes of FIG. 2B at regular intervals over time.

Referring to FIGS. 1 through 2C, the DSP 155 generates the control signal CTRL1. The control signal CTRL1 is used to control the switch SW1 to be turned on or off. The control signal CTRL1 is generated by the DSP 155 as illustrated in FIG. 1, but this is merely one example. Accordingly, the control signal CTRL1 may be generated by, for example, a signal generator (not shown). The signal generator may be located in or outside the controller 150.

The control signal CTRL1 is generated to have a period Ts.

In one example, when the switch SW1 is turned on in response to the control signal CTRL1 being activated, the power supply 110 and the first resonator 130 are connected to each other, and the first resonator 130 is charged. In this example, the first resonator 130 is charged with power output from the power supply 110 in intervals during which the control signal CTRL1 is activated.

In another example, when the switch SW1 is turned off in response to the control signal CTRL1 being deactivated, the power supply 110 and the first resonator 130 are disconnected from each other, and the first resonator 130 starts discharging. In this example, the first resonator 130 is discharged in intervals T1, T2, T3, and T4.

The first resonator 130 generates a first resonance signal RS1 through discharging in the intervals T1 through T4. When an object changes within the range of the field, a quality (Q)-factor of the first resonator 130 changes, which leads to a change in an attenuation in the generated first resonance signal RS1 over time. Examples of envelopes of the first resonance signal RS1 generated in the intervals T1 through T4 are illustrated in FIG. 2B.

The DSP 155 samples an envelope of the first resonance signal RS1 at a predetermined point in time after a falling edge FE of the control signal CTRL1, and acquires a value of the envelope of the first resonance signal RS1 at the point in time. As illustrated in FIGS. 2A and 2B, the point in time refers to a point in time at which a predetermined period of time ΔT elapses after the falling edge FE of the control signal CTRL1.

For example, in the interval T1, the DSP 155 samples an envelope of the first resonance signal RS1 at a point in time at which the period of time ΔT elapses after a falling edge FE, and acquires a value V1 of the envelope of the first resonance signal RS1. In the interval T2, the DSP 155 samples an envelope of the first resonance signal RS1 at a point in time at which the period of time ΔT elapses after a falling edge FE, and acquires a value V2 of the envelope of the first resonance signal RS1. In the interval T3, the DSP 155 samples an envelope of the first resonance signal RS1 at a point in time at which the period of time ΔT elapses after a falling edge FE, and acquires a value V3 of the envelope of the first resonance signal RS1. In the interval T4, the DSP 155 samples an envelope of the first resonance signal RS1 at a point in time at which the period of time ΔT elapses after a falling edge FE, and acquires a value V4 of the envelope of the first resonance signal RS1.

To detect the change in the object within the range of the field of the first resonator 130, the DSP 155 may detects or measures the attenuation in the first resonance signal RS1 over time based on the acquired values V1 through V4. The first resonance signal RS1 is attenuated by turning the switch SW1 off in the period Ts.

The DSP 155 calculates a period of a change in the acquired values V1 through V4 over time. To calculate the period of the change in the values V1 through V4 over time, the DSP 155 performs a Fourier transform.

The values V1 through V4 are illustrated over time in FIG. 2C. The DSP 155 acquires a waveform connecting the values V1 through V4, and calculates a change in the waveform over time.

For convenience of description, FIGS. 2A through 2C illustrate the values V1 through V4 of the envelopes acquired from the first resonance signal RS1 generated based on the control signal CTRL1 in the intervals T1 through T4, but this is merely one example. The first resonance signal RS1 may continue to be generated through a repetition of charging and discharging of the first resonator 130, and a value of an envelope of the first resonance signal RS1 may be acquired in one or more intervals after the intervals T1 through T4 as described with reference to FIG. 2B.

The DSP 155 acquires a change in a waveform connecting values of envelopes of the first resonance signal RS1 acquired in a larger number of intervals over time from the waveform, and accordingly the DSP 155 acquires a period of the change in the waveform over time. Also, the DSP 155 calculates or measures a period of a change in the attenuation in the first resonance signal RS1 over time.

Thus, the DSP 155 detects or acquires, as a period of the change in the object, a period of a change in values of envelopes of the first resonance signal RS1 acquired at regular intervals.

Based on the description of FIGS. 1 through 2C, the detecting apparatus 10A is applicable in various situations. In one example, the detecting apparatus 10A detects a biosignal from a user. In another example, when the detecting apparatus 10A is implemented or mounted in a vehicle, the detecting apparatus 10A detects a change in an object around the vehicle. In another example, when at least one detecting apparatus 10A is attached to clothes or a body of a user, the at least one detecting apparatus 10A senses a contact to a body part and recognizes a gesture.

Figure 3:
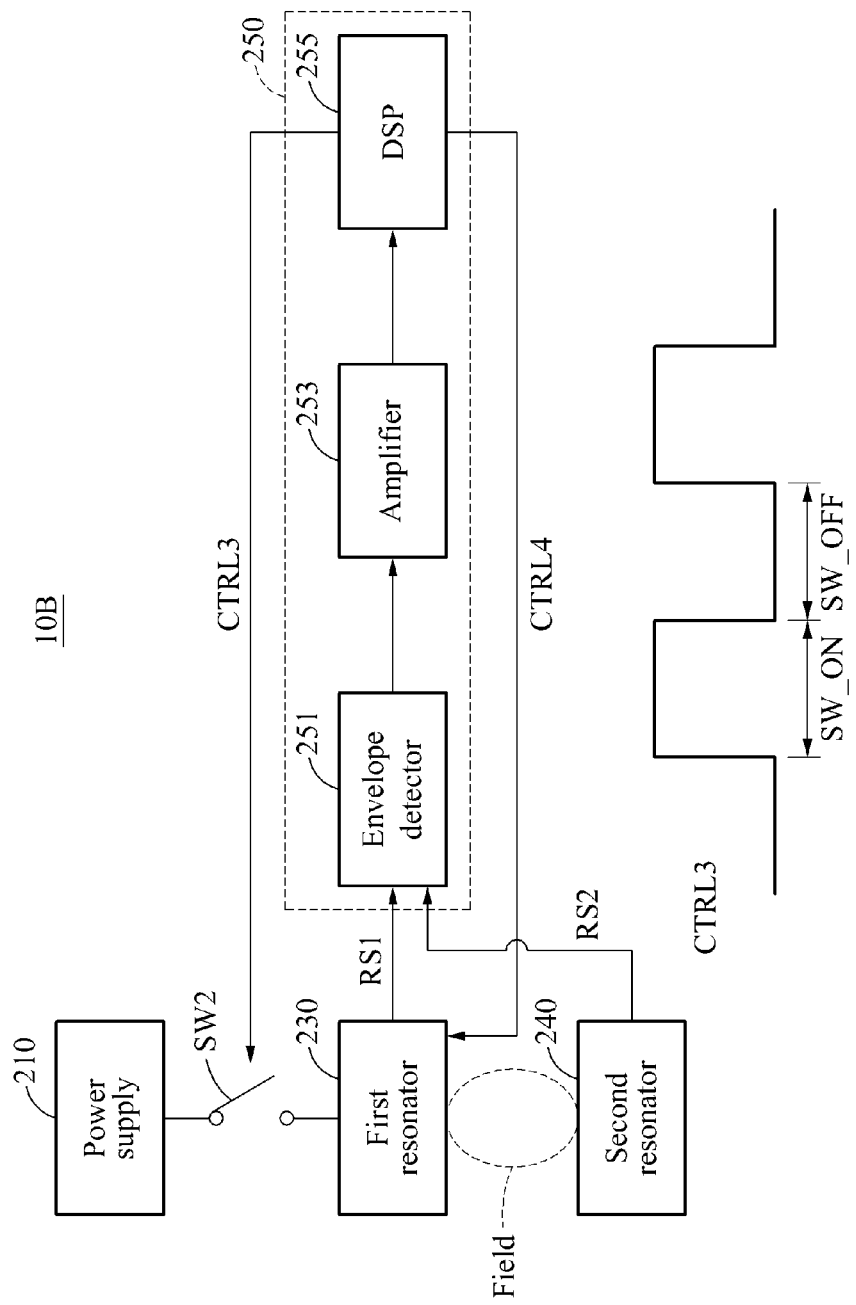
FIG. 3 illustrates another example of a detecting apparatus.

FIG. 3 illustrates another example of a detecting apparatus 10B.

Referring to FIG. 3, the detecting apparatus 10B includes a power supply 210, a switch SW2, a first resonator 230, a second resonator 240, and a controller 250. The detecting apparatus 10B is a modified version of the detecting apparatus 10A in FIG. 1.

A configuration and an operation of each of the power supply 210, the switch SW2, the first resonator 230, and the controller 250 of FIG. 3 are substantially the same as a configuration and an operation of each of the power supply 110, the switch SW1, the first resonator 130, and the controller 150 of FIG. 1. The first resonator 230 changes a resonant frequency in response to a control signal CTRL4, which is substantially the same as the control signal CTRL2 of FIG. 1.

The second resonator 240 induces a second resonance signal RS2 through a resonance between the first resonator 230 and the second resonator 240. For example, when the first resonator 230 generates a first resonance signal RS1 based on power output from the power supply 210 in response to an object changing within a range of a field of the first resonator 230, the second resonator 240 generates the second resonance signal RS2 through the resonance between the first resonator 230 and the second resonator 240.

In one example, when the switch SW2 is turned on in response to a control signal CTRL3 being activated, the power supply 210 and the first resonator 230 are connected to each other and the first resonator 230 is charged. In another example, when the switch SW2 is turned off in response to the control signal CTRL3 being deactivated, the power supply 210 and the first resonator 230 are disconnected from each other and the first resonator 230 starts discharging. In this example, the first resonator 230 generates the first resonance signal RS1 during the discharging. The second resonance signal RS2 is induced in the second resonator 240 through the resonance between the first resonator 230 and the second resonator 240.

The second resonator 240 outputs the second resonance signal RS2 to the controller 250.

The controller 250 processes either one or both of the first resonance signal RS1 and the second resonance signal RS2. The controller 250 includes an envelope detector 251, an amplifier 253, and a DSP 255.

An operation of each of the envelope detector 251, the amplifier 253, and the DSP 255 in the controller 250 to process the first resonance signal RS1 is substantially the same as that of the envelope detector 151, the amplifier 153, and the DSP 155 described with reference to FIGS. 1 through 2C. Accordingly, a description of an example in which the controller 250 processes the first resonance signal RS1 is omitted herein. Hereinafter, an example in which the controller 250 processes the second resonance signal RS2 is described.

The envelope detector 251 detects an envelope of the second resonance signal RS2. The envelope detector 251 outputs the detected envelope of the second resonance signal RS2 to the amplifier 253.

The amplifier 253 amplifies the envelope of the second resonance signal RS2. The amplifier 253 outputs the amplified envelope of the second resonance signal RS2 to the DSP 255.

The DSP 255 samples the amplified envelope of the second resonance signal RS2. The DSP 255 calculates a period of a change in a value of the envelope of the second resonance signal RS2 over time based on the sampled envelope. When an object changes within the range of the field of the first resonator 230, the DSP 255 detects or acquires the period of the change in the value of the envelope of the second resonance signal RS2 over time as a period of a change in the object.

The DSP 255 samples the envelope of the second resonance signal RS2, detects a noise component included in the second resonance signal RS2, and controls an activation time of the control signal CTRL3 based on the detected noise component. In response to the activation time of the control signal CTRL3 being controlled, the range of the field of the first resonator 230 is adjusted. In one example, when the activation time of the control signal CTRL3 is controlled to increase, the first resonator 230 is connected to the power supply 210 during a relatively long period of time, is charged with a large amount of power or energy, and generates a first resonance signal RS1 with a greater magnitude so that a second resonance signal RS2 with a greater magnitude is induced in the second resonator 240. In another example, when the activation time of the control signal CTRL3 is controlled to decrease, the first resonator 230 is connected to the power supply 210 during a relatively short period of time, is charged with a small amount of power or energy, and generates a first resonance signal RS1 with a smaller magnitude so that a second resonance signal RS2 with a smaller magnitude is induced in the second resonator 240.

Hereinafter, an operating method of the detecting apparatus 10B to process the second resonance signal RS2 in order to detect a change in an object within the range of the field of the first resonator 230 is further described with reference to FIGS. 4A, 4B, and 4C.

Figure 4C:
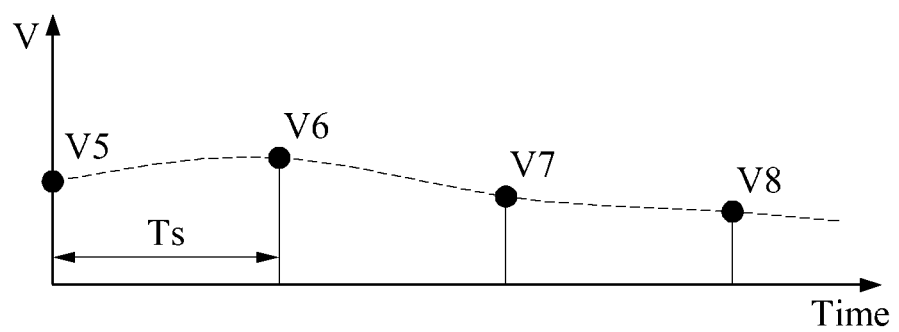
FIG. 4C is a graph provided to explain an example of a period of a change in maximum values of envelopes of the second resonance signal of FIG. 4B over time.

FIG. 4A is a timing diagram of an example of the control signal CTRL3 output to the switch SW3 of FIG. 3, and FIG. 4B is a graph provided to explain examples of envelopes of a first resonance signal and a second resonance signal generated based on the control signal CTRL3 of FIG. 4A. FIG. 4C is a graph provided to explain an example of a period of a change in maximum values of envelopes of the second resonance signal of FIG. 4B over time.

Referring to FIGS. 3 through 4C, the DSP 255 generates the control signal CTRL3. The control signal CTRL3 is used to control the switch SW2 to be turned on or off. The control signal CTRL3 is generated by the DSP 255 as illustrated in FIG. 3, but this is merely one example. Accordingly, the control signal CTRL3 may be generated by, for example, a signal generator (not shown). The signal generator may be located in or outside the controller 250.

The control signal CTRL3 is generated to have a period Ts.

In one example, when the switch SW2 is turned on in response to the control signal CTRL3 being activated, the power supply 210 and the first resonator 230 are connected to each other, and the first resonator 230 is charged. In this example, the first resonator 230 is charged with power output from the power supply 210 in intervals during which the control signal CTRL1 is activated.

In another example, when the switch SW2 is turned off in response to the control signal CTRL3 being deactivated, the power supply 210 and the first resonator 230 are disconnected from each other, and the first resonator 230 starts discharging. In this example, the first resonator 1230 is discharged in intervals T1, T2, T3, and T4.

The first resonator 230 generates a first resonance signal RS1 through discharging in the intervals T1 through T4. The second resonance signal RS2 is induced in the second resonator 240 through a resonance between the first resonator 230 and the second resonator 240 in the intervals T1 through T4. When an object changes within the range of the field of the first resonator 230, a coupling characteristic between the first resonator 230 and the second resonator 240 changes, which leads to a change in a magnitude of the second resonance signal RS2 induced in the second resonator 240. Envelopes of the first resonance signal RS1 and the second resonance signal RS2 generated in the intervals T1 through T4 are illustrated in FIG. 4B.

The DSP 255 acquires maximum values of envelopes of the second resonance signal RS2 by sampling the envelopes of the second resonance signal RS2 in an interval during which the control signal CTRL3 is deactivated. Referring to FIG. 4A, in an interval from a falling edge FE of the control signal CTRL3 to a positive edge PE of the control signal CTRL3, the DSP 255 acquires a maximum value of an envelope of the second resonance signal RS2 by sampling the envelope of the second resonance signal RS2.

For example, in the interval T1, the DSP 255 samples an envelope of the second resonance signal RS2 and acquires a maximum value V5 of the envelope. In the interval T2, the DSP 255 samples an envelope of the second resonance signal RS2 and acquires a maximum value V6 of the envelope. In the interval T3, the DSP 255 samples an envelope of the second resonance signal RS2 and acquires a maximum value V7 of the envelope. In the interval T4, the DSP 255 samples an envelope of the second resonance signal RS2 and acquires a maximum value V8 of the envelope.

The DSP 255 detects the change in the object within the range of the field of the first resonator 230 based on the acquired maximum values V5 through V8.

The DSP 255 calculates a period of a change in the acquired maximum values V5 through V8 over time. To calculate the period of the change in the maximum values V5 through V8 over time, the DSP 255 performs a Fourier transform.

The maximum values V5 through V8 are illustrated over time in FIG. 4C. The DSP 255 acquires a waveform connecting the maximum values V5 through V8, and calculates a change in the waveform over time.

For convenience of description, FIGS. 4A through 4C illustrate the maximum values V5 through V8 of the envelopes acquired from the second resonance signal RS2 generated based on the control signal CTRL3 in the intervals T1 through T4, but this is merely one example. The second resonance signal RS2 may continue to be induced through a repetition of charging and discharging of the first resonator 230, and a maximum value of an envelope of the second resonance signal RS2 may be acquired in one or more intervals after the intervals T1 through T4 as described with reference to FIG. 4B.

The DSP 255 acquires a change in a waveform connecting maximum values of envelopes of the second resonance signal RS2 acquired in a larger number of intervals over time from the waveform, and accordingly the DSP 255 acquires a period of the change in the waveform over time.

Thus, the DSP 255 detects or acquires, as a period of the change in the object, a period of a change in maximum values of envelopes of the second resonance signal RS2 acquired in an interval during which the control signal CTRL3 is deactivated.

Based on the description of FIGS. 3 through 4C, the detecting apparatus 10B is applicable in various situations. In one example, the detecting apparatus 10B detects a biosignal from a user. In another example, when the detecting apparatus 10B is implemented or mounted in a vehicle, the detecting apparatus 10B detects a change in an object around the vehicle. In another example, when the detecting apparatus 10B is implemented or mounted in each of two vehicles, the detecting apparatus 10B detects a coupling change between resonators of the vehicles, and detects a distance or contact between the vehicles. In another example, when at least one detecting apparatus 10B is attached to clothes or a body of a user, the at least one detecting apparatus 10B senses a contact to a body part and recognizes a gesture.

Figure 5:
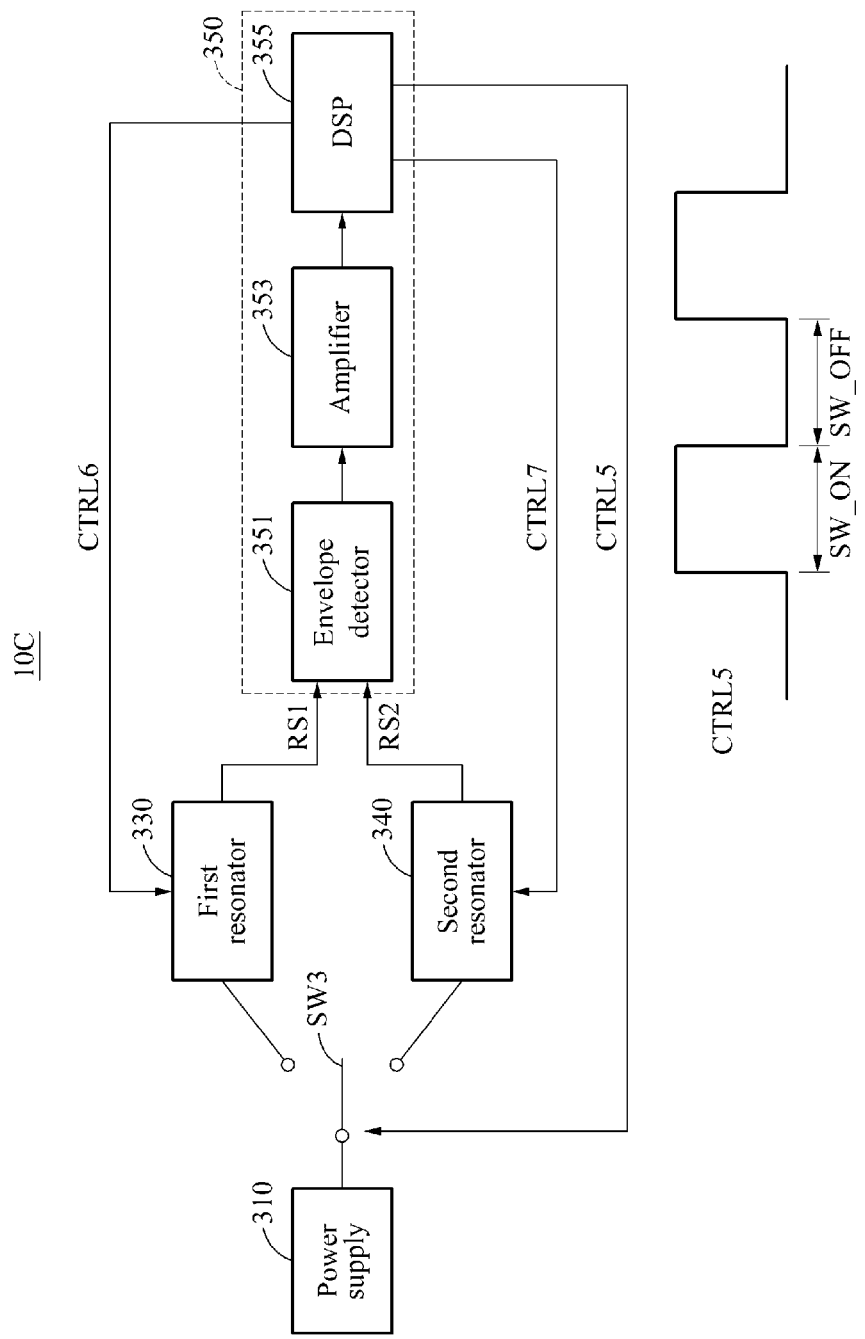
FIG. 5 illustrates another example of a detecting apparatus.

FIG. 5 illustrates another example of a detecting apparatus 10C.

Referring to FIG. 5, the detecting apparatus 10C includes a power supply 310, a switch SW3, a first resonator 330, a second resonant 340, and a controller 350. The detecting apparatus 10C is a modified version of the detecting apparatus 10A of FIG. 1.

The power supply 310 supplies power to the first resonator 330 or the second resonator 340. In one example, when the power supply 310 is connected to the first resonator 330 via the switch SW3, the power supply 310 supplies power to the first resonator 130. In another example, when the power supply 310 is connected to the second resonator 340 via the switch SW3, the power supply 310 supplies power to the second resonator 340.

The switch SW3 is turned on or off in response to a control signal CTRL5. For example, the switch SW3 is turned on in response to the control signal CTRL5 being activated, as indicated by SW_ON of FIG. 5, and is turned off in response to the control signal CTRL5 being deactivated, as indicated by SW_OFF of FIG. 5.

The switch SW3 controls a connection between the power supply 310 and one of the first resonator 330 and the second resonator 340 in response to the control signal CTRL5.

The controller 350 processes either a first resonance signal RS1 or a second resonance signal RS2. The first resonance signal RS1 and the second resonance signal RS2 are generated by the first resonator 330 and the second resonator 340, respectively. For example, the controller 350 samples a value of an envelope of either the first resonance signal RS1 or the second resonance signal RS2.

A configuration and an operation of each of the power supply 310, the switch SW3, the first resonance signal RS1, the second resonance signal RS2, and the controller 350 of FIG. 5 may be substantially the same as a configuration and an operation of each of the power supply 110, the switch SW1, the first resonator 130, and the controller 150 of FIG. 1. The first resonator 330 changes a resonant frequency in response to a control signal CTRL6, which is substantially the same as the control signal CTRL2 of FIG. 1. The second resonator 340 changes a resonant frequency in response to a control signal CTRL7, which is substantially the same as the control signal CTRL2 of FIG. 1.

The first resonator 330 may be implemented as a resonator configured to generate an electric field in the form of a capacitor, or a resonator configured to generate a magnetic field in the form of an inductor. Also, the second resonator 340 may be implemented as a resonator configured to generate an electric field in the form of a capacitor, or a resonator configured to generate a magnetic field in the form of an inductor. The resonator configured to generate an electric field in the form of a capacitor is suitable to detect a change in a dielectric constant of an object within a range of the electric field. The resonator configured to generate a magnetic field in the form of an inductor is suitable to detect a change in a permeability of an object within a range of the magnetic field.

The first resonator 330 and the second resonator 340 may be configured to generate different fields. By selectively using one of resonators with different ratios in a magnitude between an electric field and a magnetic field using the switch SW3, the detecting apparatus 10C may selectively detect a change in a characteristic of the object, for example, a permeability or dielectric constant of the object.

Figure 7:
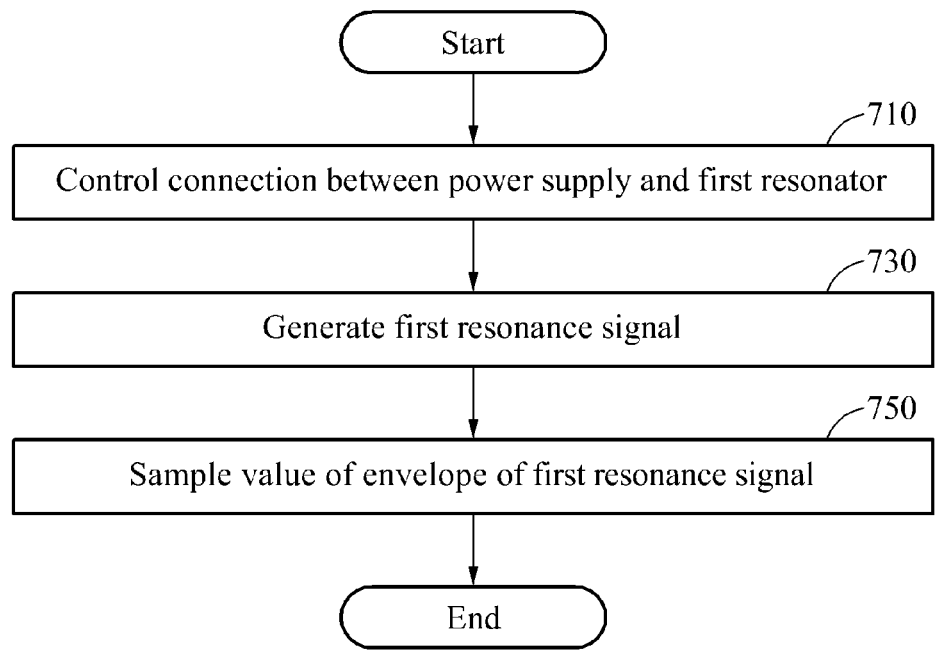
FIG. 7 illustrates an example of an operating method of the detecting apparatus of FIG. 1.

FIG. 7 illustrates an example of an operating method of the detecting apparatus 10A of FIG. 1.

Referring to FIGS. 1 through 2C and 7, in operation 710, the switch SW1 controls a connection between the power supply 110 and the first resonator 130 in response to the control signal CTRL1.

When an object changes within the range of the field, the first resonator 130 generates the first resonance signal RS1 based on the power output from the power supply 110 in operation 730.

In operation 750, the controller 150 samples a value of the envelope of the first resonance signal RS1.

Figure 8:
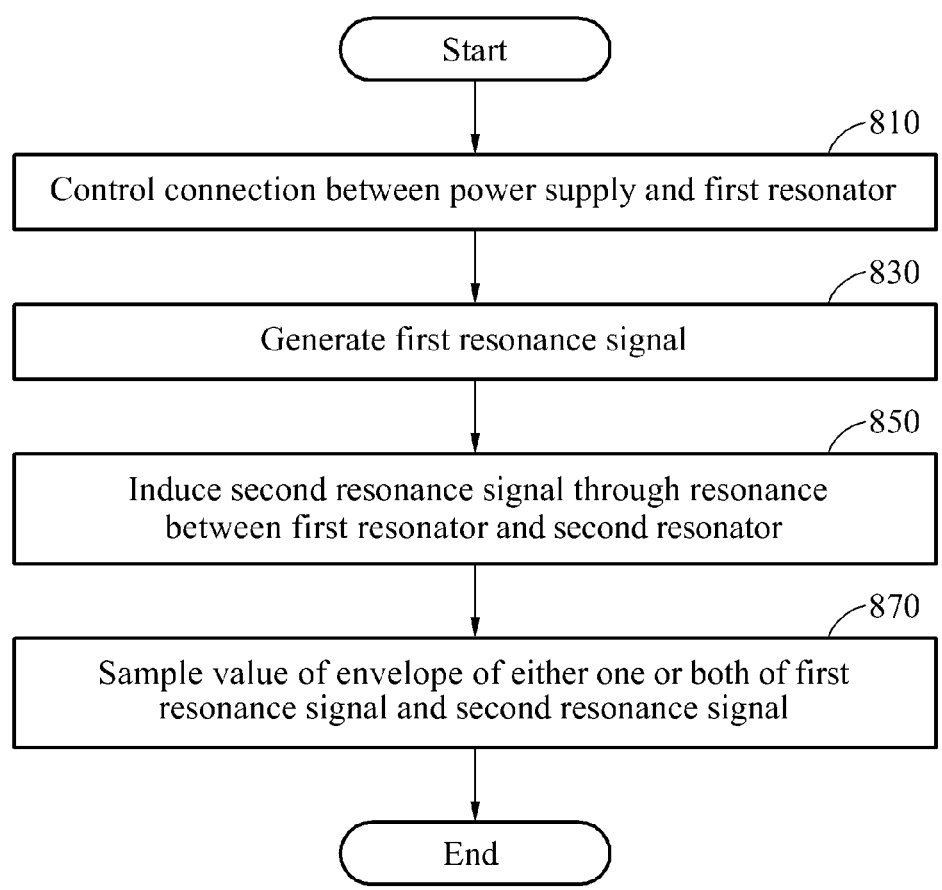
FIG. 8 illustrates an example of an operating method of the detecting apparatus of FIG. 3.

FIG. 8 illustrates an example of an operating method of the detecting apparatus 10B of FIG. 3.

Referring to FIGS. 3 through 4C and 8, in operation 810, the switch SW2 controls a connection between the power supply 210 and the first resonator 230 in response to the control signal CTRL3.

When an object changes within the range of the field, the first resonator 230 generates the first resonance signal RS1 based on the power output from the power supply 210 in operation 830.

In operation 850, the second resonance signal RS2 is induced in the second resonator 240 through the resonance between the first resonator 230 and the second resonator 240.

In operation 870, the controller 250 samples a value of an envelope of either one or both of the first resonance signal RS1 and the second resonance signal RS2.

Figure 9:
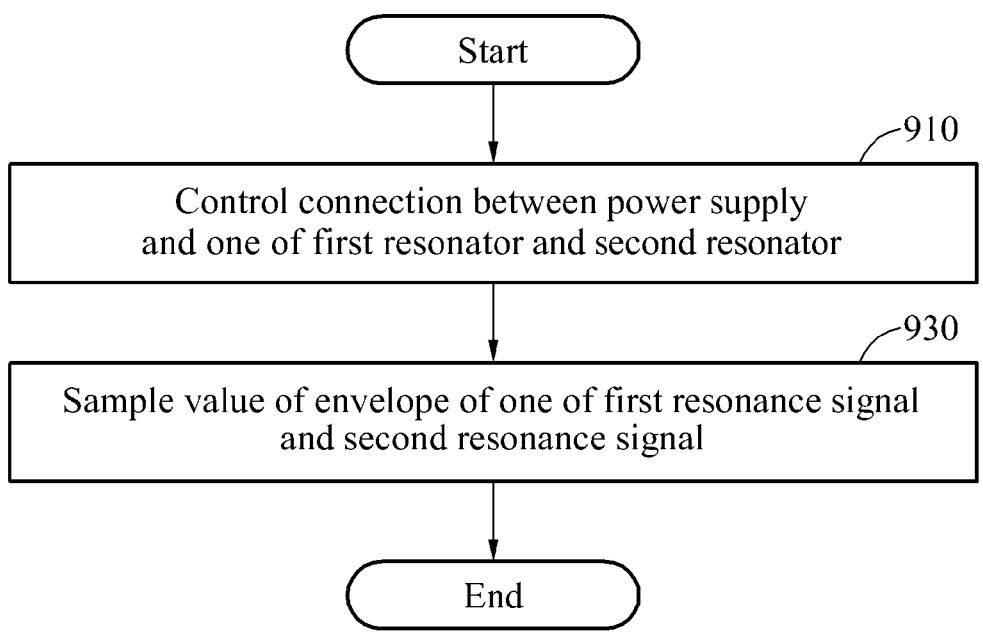
FIG. 9 illustrates an example of an operating method of the detecting apparatus of FIG. 5.

FIG. 9 illustrates an example of an operating method of the detecting apparatus 10C of FIG. 5.

Referring to FIGS. 5 and 9, in operation 910, the switch SW3 controls a connection between the power supply 310 and one of the first resonator 330 and the second resonator 340 in response to the control signal CTRL5.

In operation 930, the controller 350 samples a value of an envelope of one of the first resonance signal RS1 and the second resonance signal RS2 that are generated by the first resonator 330 and the second resonator 340, respectively.

Figure 10:
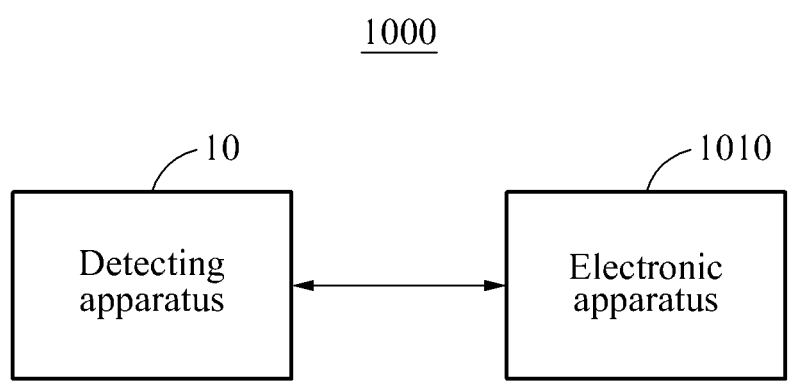
FIG. 10 illustrates an example of an electronic system including a detecting apparatus.

FIG. 10 illustrates an example of an electronic system 1000 including a detecting apparatus 10.

Referring to FIG. 10, the electronic system 1000 includes the detecting apparatus 10 and an electronic apparatus 1010. The detecting apparatus 10 may be the detecting apparatus 10A of FIG. 1, the detecting apparatus 10B of FIG. 3, or the detecting apparatus 10C of FIG. 5.

The electronic apparatus 1010 may be implemented as a PC, a data server, or a portable apparatus.

The portable apparatus may be implemented as a laptop computer, a mobile phone, a smart phone, a tablet PC, an MID, a PDA, an EDA, a digital still camera, a digital video camera, a PMP, a PND, a handheld game console, an e-book, or a smart device.

The smart device may be implemented as a smart watch or a smart band.

The electronic apparatus 1010 may be wearable by a user. The electronic apparatus 1010 may include, for example, all wearable devices capable of or suitable for being worn by users.

The detecting apparatus 10 and the electronic apparatus 1010 communicate with each other.

Figure 11:
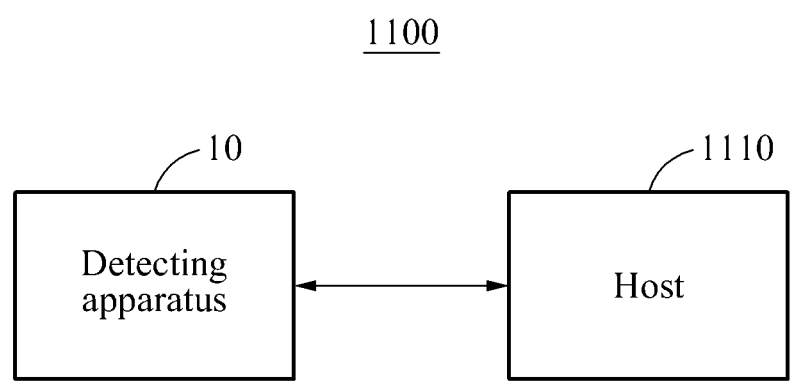
FIG. 11 illustrates another example of an electronic system including a detecting apparatus.

FIG. 11 illustrates another example of an electronic system 1100 including a detecting apparatus 10.

Referring to FIG. 11, the electronic system 1100 includes the detecting apparatus 10 and a host 1110. The detecting apparatus 10 may be the detecting apparatus 10A of FIG. 1, the detecting apparatus 10B of FIG. 3, or the detecting apparatus 10C of FIG. 5.

The detecting apparatus 10 includes, for example, a patient monitor, an ECG device, a respiratory rate sensor, a pulse rate sensor, a body temperature sensor, an electric conduction sensor, or a medical imaging device, in addition to those described with reference to FIG. 1.

The host 1110 and the detecting apparatus 10 communicate with each other. For example, the host 1110 and the detecting apparatus 10 may interoperate with each other. The host 1110 may control the detecting apparatus 10, or the detecting apparatus 10 may control the host 1110.

The host 1110 may be implemented as a portable electronic apparatus. The portable electronic apparatus may be implemented as a laptop computer, a mobile phone, a smart phone, a tablet PC, an MID, a PDA, an EDA, a digital still camera, a digital video camera, a PMP, a PND, a handheld game console, an e-book, or a smart device.

The smart device may be implemented as a smart watch or a smart band.

The host 1110 continues to monitor, using the detecting apparatus 10, a state of a user wearing the detecting apparatus 10 or a change in the user. The state of the user may be a health state, a physiological condition, or a medical state of the user.

Figure 12:
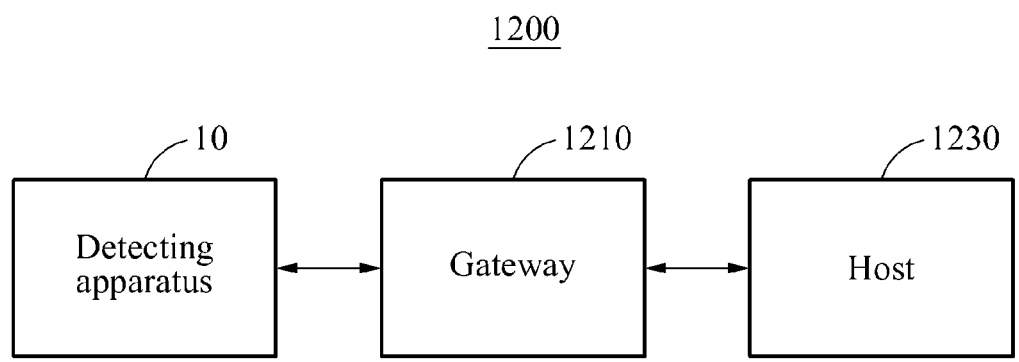
FIG. 12 illustrates another example of an electronic system including a detecting apparatus.

FIG. 12 illustrates another example of an electronic system 1200 including a detecting apparatus 10.

Referring to FIG. 12, the electronic system 1200 includes the detecting apparatus 10, a gateway 1210, and a host 1230. The electronic system 1200 may be, for example, a health monitoring system. The detecting apparatus 10 may be the detecting apparatus 10A of FIG. 1, the detecting apparatus 10B of FIG. 3, or the detecting apparatus 10C of FIG. 5.

The detecting apparatus 10 and the host 1230 communicate with each other through the gateway 1210.

The gateway 1210 may be implemented as a portable electronic apparatus. The portable electronic apparatus may be implemented as a laptop computer, a mobile phone, a smart phone, a tablet PC, an MID, a PDA, an EDA, a digital still camera, a digital video camera, a PMP, a PND, a handheld game console, an e-book, or a smart device.

The smart device may be implemented as a smart watch or a smart band.

The host 1230 may be, for example, a medical system of a medical institution.

The controllers 150, 250, and 350, the envelope detectors 151, 251, and 351, the amplifiers 153, 253, and 353, and the DSPs 155, 255, and 355 in FIGS. 1, 3, and 5 that perform the operations described herein with respect to FIGS. 1-12 are implemented by hardware components. Examples of hardware components include controllers, generators, drivers, memories, comparators, arithmetic logic units, adders, subtractors, multipliers, dividers, integrators, analog-to-digital (A/D) converters, digital-to-analog (D/A) converters, amplifiers, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1-12. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 7-9 that perform the operations described herein with respect to FIGS. 1-6 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A detecting apparatus comprising:
    a first resonator configured to generate a first resonance signal based on power output from a power supply in response to an object changing within a range of a field of the first resonator;
    a switch configured to connect the first resonator to the power supply in response to a control signal; and
    a controller configured to sample a value of an envelope of the first resonance signal and detect an attenuation in the first resonance signal over time to detect a change in the object wherein the controller is configured to control an amount of energy of the first resonator, a magnitude of the first resonance signal, and the range of the field of the first resonator based on the noise component of the first resonance signal.

2. The detecting apparatus of claim 1, wherein the controller is further configured to sample the envelope of the first resonance signal at a predetermined point in time after a falling edge of the control signal, and acquire a value of the envelope of the first resonance signal at the predetermined point in time.

3. The detecting apparatus of claim 2, wherein the controller is further configured to calculate a period of a change in the acquired value of the envelope of the first resonance signal over time.

4. The detecting apparatus of claim 1, further comprising a second resonator configured to induce a second resonance signal through a resonance between the first resonator and the second resonator;
    wherein the controller is further configured to sample a value of an envelope of the second resonance signal to detect the change in the object.

5. The detecting apparatus of claim 4, wherein the controller is further configured to acquire a maximum value of the envelope of the second resonance signal by sampling the envelope of the second resonance signal in response to the control signal being deactivated.

6. The detecting apparatus of claim 5, wherein the controller is further configured to calculate a period of a change in the acquired maximum value of the envelope of the second resonance signal over time.

7. The detecting apparatus of claim 1, wherein the controller is further configured to change a resonant frequency of the first resonator to control the range of the field.

8. The detecting apparatus of claim 1, wherein the controller is further configured to sample the envelope of the first resonance signal, detect a noise component included in the first resonance signal, and control an activation time of the control signal based on the noise component.

9. The detecting apparatus of claim 1, further comprising a second resonator configured to induce a second resonance signal based on the power output from the power supply;

wherein the switch is further configured to connect one of the first resonator and the second resonator to the power supply in response to the control signal; and the controller is further configured to sample a value of an envelope of a resonance signal output from one of the first resonator and the second resonator to detect the change in the object.

10. A detecting apparatus comprising:
a first resonator configured to generate a first resonance signal based on power output from a power supply in response to an object changing within a range of a field of the first resonator;
a switch configured to connect the first resonator to the power supply in response to a control signal;
a second resonator configured to induce a second resonance signal through a resonance between the first resonator and the second resonator; and
a controller configured to sample a value of an envelope of either one or both of the first resonance signal and the second resonance signal and detect an attenuation in the first resonance signal over time to detect a change in the object and control an amount of energy of the first resonator, a magnitude of the first resonance signal, and the range of the field of the first resonator based on the noise component of the first resonance signal.

11. The detecting apparatus of claim 10, wherein the controller is further configured to sample an envelope of the first resonance signal at a predetermined point in time after a falling edge of the control signal, and acquire a value of the envelope of the first resonance signal at the predetermined point in time.

12. The detecting apparatus of claim 10, wherein the controller is further configured to acquire a maximum value of an envelope of the second resonance signal by sampling the envelope of the second resonance signal in response to the control signal being deactivated.

13. The detecting apparatus of claim 10, wherein the controller is further configured to change a resonant frequency of the first resonator to control the range of the field.

14. The detecting apparatus of claim 10, wherein the controller is further configured to sample an envelope of either one or both of the first resonance signal and the second resonance signal to detect a noise component included in either one or both of the first resonance signal and the second resonance signal, and control an activation time of the control signal based on the noise component.

15. A method of detecting a change in an object, the method comprising:
connecting a first resonator to a power supply in response to a control signal;
generating, using the first resonator, a first resonance signal based on power output from the power supply in response to the object changing within a range of a field of the first resonator;
sampling a value of an envelope of the first resonance signal; and detecting an attenuation in the first resonance signal over time; and control an amount of energy of the first resonator, a magnitude of the first resonance signal, and the range of the field of the first resonator based on the noise component of the first resonance signal.

16. The method of claim 15, wherein the sampling comprises:
sampling the envelope of the first resonance signal at a predetermined point in time after a falling edge of the control signal; and
acquiring a value of the envelope of the first resonance signal at the predetermined point in time.

17. The method of claim 16, further comprising calculating a period of a change in the acquired value of the envelope over time.

18. The method of claim 15, further comprising:
inducing a second resonance signal, using a second resonator, through a resonance between the first resonator and the second resonator; and
sampling a value of an envelope of the second resonance signal to detect the change in the object.

19. The method of claim 18, wherein the sampling of the value of the envelope of the second resonance signal comprises acquiring a maximum value of the envelope of the second resonance signal by sampling the envelope of the second resonance signal in response to the control signal being deactivated.

20. The method of claim 19, further comprising calculating a period of a change in the acquired maximum value of the envelope of the second resonator over time.

* * * * *